(12) United States Patent
Chen et al.

(10) Patent No.: US 12,078,592 B2
(45) Date of Patent: Sep. 3, 2024

(54) MID-INFRARED GAS SENSOR BASED ON TAPERED SUB-WAVELENGTH GRATING SLOT WAVEGUIDE

(71) Applicant: Ningbo University, Zhejiang (CN)

(72) Inventors: Weiwei Chen, Zhejiang (CN); Yuefeng Wang, Zhejiang (CN); Pengjun Wang, Zhejiang (CN); Dong Zhang, Zhejiang (CN); Yan Li, Zhejiang (CN)

(73) Assignee: Ningbo University, Zhejiang (CN)

( * ) Notice: Subject to any disclaimer, the term of this patent is extended or adjusted under 35 U.S.C. 154(b) by 248 days.

(21) Appl. No.: 17/898,457

(22) Filed: Aug. 29, 2022

(65) Prior Publication Data
US 2023/0393060 A1 Dec. 7, 2023

(30) Foreign Application Priority Data
Jun. 2, 2022 (CN) .......................... 202210621443.7

(51) Int. Cl.
*G01N 21/3504* (2014.01)
*G01N 33/00* (2006.01)

(52) U.S. Cl.
CPC ..... *G01N 21/3504* (2013.01); *G01N 33/0027* (2013.01); *G01N 2201/0635* (2013.01)

(58) Field of Classification Search
None
See application file for complete search history.

(56) References Cited

U.S. PATENT DOCUMENTS

| 5,701,008 A | * | 12/1997 | Ray | G01J 5/0875 |
| | | | | 250/353 |
| 2021/0116433 A1 | * | 4/2021 | Weng | G01N 33/0044 |

FOREIGN PATENT DOCUMENTS

| CN | 101923051 A | * | 12/2010 |
| CN | 102235969 B | * | 5/2013 |
| CN | 106024931 A | * | 10/2016 |

OTHER PUBLICATIONS

Mingquan PI, et al., "Design of a mid-infrared suspended chalcogenide/silica-on-silicon slot-waveguide spectroscopic gas sensor with enhanced light-gas interaction effect," Sensors and Actuators B: Chemical, vol. 297, 126732, Oct. 2019, pp. 1-11.

(Continued)

*Primary Examiner* — Marcus H Taningco
(74) *Attorney, Agent, or Firm* — JCIPRNET

(57) ABSTRACT

A mid-infrared gas sensor based on a tapered sub-wavelength grating slot waveguide comprises a lower cladding, a first tapered grating array and a second tapered grating array. The first tapered grating array and the second tapered grating array are disposed on an upper surface of the lower cladding. The first tapered grating array is located in front of the second tapered grating array. The first tapered grating array is formed by 5566 identical first core waveguides that are regularly distributed at intervals from left to right. The second tapered grating array is formed by 5566 identical second core waveguides that are regularly distributed at intervals from left to right. The first core waveguides and the second core waveguides are tapered waveguides. Upper sides and lower sides of the first core waveguides and the second core waveguides are isosceles trapezoids.

1 Claim, 3 Drawing Sheets

(56) References Cited

OTHER PUBLICATIONS

Yuefeng Wang, et al., "Ultra-high-power-confinement-factor integrated mid-infrared gas sensor based on the suspended slot chalcogenide glass waveguide," Sensors and Actuators B: Chemical, vol. 347, 130466, Nov. 2021, pp. 1-8.

Antoine Gervais, et al., "Design of Slow-Light Subwavelength Grating Waveguides for Enhanced On-Chip Methane Sensing by Absorption Spectroscopy," IEEE Journal of Selected Topics in Quantum Electronics, vol. 25, No. 3, May-Jun. 2019, pp. 1-8.

Guizhen Xu, et al., "Design and analysis of slow-light Bloch slot waveguides for on-chip gas sensing," Journal of the Optical Society of America B, vol. 37, No. 2, Feb. 2020, pp. 257-263.

Babita Kumari, et al., "Design of chip scale silicon rib slot waveguide for sub-ppm detection of N2O gas at mid-IR band," Sensors and Actuators B: Chemical, vol. 255, Part 3, Feb. 2018, pp. 3409-3416.

* cited by examiner

MID-INFRARED GAS SENSOR BASED ON TAPERED SUB-WAVELENGTH GRATING SLOT WAVEGUIDE

CROSS-REFERENCE TO RELATED APPLICATION

This application claims the priority benefit of China application no. 202210621443.7, filed on Jun. 2, 2022. The entirety of the above-mentioned patent application is hereby incorporated by reference and made a part of this specification.

BACKGROUND OF THE INVENTION

1. Technical Field

The invention relates to a mid-infrared gas sensor, in particular to a mid-infrared gas sensor based on a tapered sub-wavelength grating slot waveguide.

2. Description of Related Art

The development of new industrial technologies is accompanied by more serious environmental pollution caused by frequent human activities. With the steady improvement of people's health and safety awareness, effective online monitoring and accurate fast warning of poisonous, harmful, flammable and explosive gases have become the basic assurance of life and property security of the masses. Moreover, the high-precision requirements of the techniques such as medical detection, deep-sea work and space exploration directly lead the development trend of small, integrated and high-precision sensors.

Gas sensors, used for gas detection, are applied to many scenarios such as environmental quality monitoring, and play an important role in energy exploitation and clinical care. There are many types of gas sensors on the market, and by principle, these gas sensors are classified into: catalytic combustion-based gas sensors, semiconductor gas sensors, thermal conductivity detection-based gas sensors, electrochemical gas sensors, and optical gas sensors. The catalytic combustion-based gas sensors, the semiconductor gas sensors, the thermal conductivity detection-based gas sensors and the electrochemical gas sensors, as traditional gas sensors, are generally based on various physical properties and chemical reactions, and adopt contact measurement, which is unsatisfying in long-term stability and high in calibration frequency, and sensitive elements in such gas sensors is short in service life. The optical gas sensor, as a novel gas sensor, senses the variation of light wave parameters such as light intensity, frequency, polarization and phase in cooperation with a light source and a photoelectric detector, to fulfill the purpose of gas detection. Compared with the other types of traditional gas sensors, the optical gas sensor adopts non-contact measurement, can resist electromagnetic interference and is free of cross sensitivity, thus exactly overcoming the defects of short service life and unsatisfying stability of the other types of traditional gas sensors. Of all existing optical gas sensors, gas sensors based on spectral absorption develop most rapidly. The gas sensors based on spectral absorption carry out measurement and analysis based on the characteristic absorption spectrum of substance molecules under different wavelengths, and the type and concentration of gas can be determined by measuring the transmission intensity of the spectrum. With the development of the micro-nano photonic devices, long-path optical fiber platforms of the gas sensors based on spectral absorption have been gradually transformed into small-sized waveguide platforms to realize a small size and an integration property. In terms of existing study, the performance parameters such as sensitivity, detection threshold and response time of the gas sensors based on spectral absorption still need to be improved.

BRIEF SUMMARY OF THE INVENTION

The technical issue to be settled by the invention is to provide a mid-infrared gas sensor based on a tapered sub-wavelength grating slot waveguide, which is high in sensitivity, low in detection threshold and quick in response.

The technical solution adopted by the invention to settle the above technical issue is as follows: a mid-infrared gas sensor based on a tapered sub-wavelength grating slot waveguide comprises a lower cladding, a first tapered grating array and a second tapered grating array, wherein the lower cladding is a cuboid waveguide and is made of calcium fluoride. A length direction of the lower cladding is a left-right direction, a width direction of the lower cladding is a front-back direction, a thickness direction of the lower cladding is an up-down direction, the lower cladding has a thickness greater than or equal to 6 μm, the first tapered grating array and the second tapered grating array are disposed on an upper surface of the lower cladding, and the first tapered grating array is located in front of the second tapered grating array. The first tapered grating array is formed by m identical first core waveguides that are regularly distributed at intervals from left to right, the value of m is 5566. The first core waveguides are tapered waveguides and are made of silicon. Front faces of the first core waveguides are rectangular. Long edges of the front faces of the first core waveguides are in the left-right direction. Wide edges of the front faces of the first core waveguides are in the up-down direction. The long edges of the front faces of the first core waveguides have a length of 784 nm. The wide edges of the front faces of the first core waveguides have a width of 6 μm. Long edges of rear faces of the first core waveguides are in the left-right direction. Wide edges of the rear faces of the first core waveguides is in the up-down direction. The long edges of the rear faces of the first core waveguides have a length of 980 nm. The wide edges of the rear faces of the first core waveguides have a width of 6 μm. Each first core waveguide has four sides. A distance between the front faces and rear faces of the first core waveguides is 1.6 μm. An upper side and a lower side of each first core waveguide are both isosceles trapezoids with a upper base of 784 nm. A lower base of 980 nm and a height of 1.6 μm. Left and right sides of the first core waveguides are rectangular. Wide edges of the left and right sides of the first core waveguides are in the up-down direction and have a width of 6 μm. Two long edges of the left side of each first core waveguide coincide with a left hypotenuse of the upper side of the first core waveguide and a left hypotenuse of the lower side of the first core waveguide in a one-to-one corresponding manner. Two long edges of the right side of each first core waveguide coincide with a right hypotenuse of the upper side of the first core waveguide and a right hypotenuse of the lower side of the first core waveguide in a one-to-one corresponding manner. The front faces of the m first core waveguides are located on a same plane. The rear faces of the m first core waveguides are located on a same plane, the plane where the front faces of the m first core waveguides are located is parallel to a front face of the lower cladding. A distance from a bilateral symmetry plane of a leftmost first core waveguide of the m first core waveguides to a left face of the lower cladding is greater than or equal to 980 nm. A distance from a bilateral symmetry plane of a rightmost first core waveguide to a right face of the lower cladding is greater than or equal to 980 nm, and a distance between the bilateral symmetry planes of every two adjacent first core waveguides is 1960 nm. The second tapered grating array is formed by m identical second core waveguides that are regularly distributed at intervals from left to right, the value of m is 5566. The second core waveguides are tapered waveguides and are made of silicon. Rear faces of the second core waveguides are rectangular. Long edges of the rear faces of the second core waveguides are in the left-right direction. Wide edges of the rear faces of the second core waveguides are in the up-down direction. The long edges of the rear faces of the second core waveguides have a length of 784 nm. The wide edges of the rear faces of the second core waveguides have a width of 6 µm. Long edges of front faces of the second core waveguides are in the left-right direction. Wide edges of the front faces of the second core waveguides are in the up-down direction. The long edges of the front faces of the second core waveguides have a length of 980 nm. The wide edges of the front faces of the second core waveguides have a width of 6 µm. A distance between the front faces and the rear faces of the second core waveguides is 1.6 µm. Each second core waveguide has four sides, an upper side and a lower side of each second core waveguide are both isosceles trapezoids with an upper base of 784 nm. A lower base of 980 nm and a height of 1.6 µm, left and right sides of the second core waveguides are rectangular. Wide edges of the left and right sides of the second core waveguides are in the up-down direction and have a width of 6 µm. Two long edges of the left side of each second core waveguide coincide with a left hypotenuse of the upper side of the second core waveguide and a left hypotenuse of the lower side of the second core waveguide in a one-to-one corresponding manner. Two long edges of the right side of each second core waveguide coincide with a right hypotenuse of the upper side of the second core waveguide and a right hypotenuse of the lower side of the second core waveguide in a one-to-one corresponding manner. The front faces of the m second core waveguides are located on a same plane. The rear faces of the m second core waveguides are located on a same plane. The plane where the rear faces of the m second core waveguides are located is parallel to the rear face of the lower cladding, a distance from a bilateral symmetry plane of a leftmost second core waveguide of the m second core waveguides to the left face of the lower cladding is greater than or equal to 980 nm. A distance from a bilateral symmetry plane of a rightmost second core waveguide to the right face of the lower cladding is greater than or equal to 980 nm, and a distance between the bilateral symmetry planes of every two adjacent second core waveguides is 1960 nm. A distance from the plane where the front faces of the m second core waveguides are located to the plane where the rear faces of the m first core waveguides are located is 120 nm; and a distance from the plane where the front faces of the m first core waveguides are located to the front face of the lower cladding is equal to a distance from the plane where the rear faces of the m second core waveguides are located to the rear face of the lower cladding, and is greater than or equal to 11.55 µm. Compared with the prior art, the invention has the following advantages: the mid-infrared gas sensor is composed of a lower cladding, a first tapered grating array and a second tapered grating array, the first tapered grating array and the second tapered grating array are disposed on an upper surface of the lower cladding, the first tapered grating array is located in front of the second tapered grating array, the first tapered grating array is formed by 5566 identical first core waveguides that are regularly distributed at intervals from left to right, the second tapered grating array is formed by 5566 identical second core waveguides that are regularly distributed at intervals from left to right, the first core waveguides and the second core waveguides are all tapered waveguides, and upper sides and lower sides of the first core waveguides and the second core waveguides are isosceles trapezoids, so that light-substance interaction areas at the position of the first tapered grating array and at the position of the second tapered grating array are effectively enlarged, the light-substance interaction energy density is increased, thus obtaining a large dimensionless parameter of light-substance interaction. With the enhancement of the light-substance interaction, more light will participate in sensing, so that the sensing sensitivity and the detection threshold are further improved. Compared with similar sensor devices, the length of an effective light path is further decreased, so that a response can be given more rapidly. Therefore, the mid-infrared gas sensor is high in sensitivity, low in detection threshold and quick in response.

DETAILED DESCRIPTION OF THE INVENTION

The invention will be described in further detail below in conjunction with the accompanying drawings and embodiments.

Figure 1:
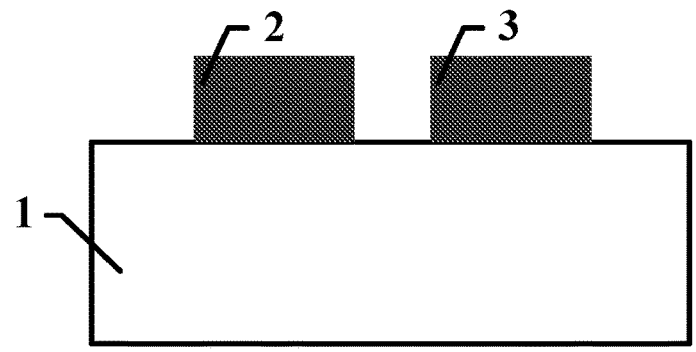
FIG. 1 is a left view of a mid-infrared gas sensor based on a tapered sub-wavelength grating slot waveguide according to the invention.
Figure 2:
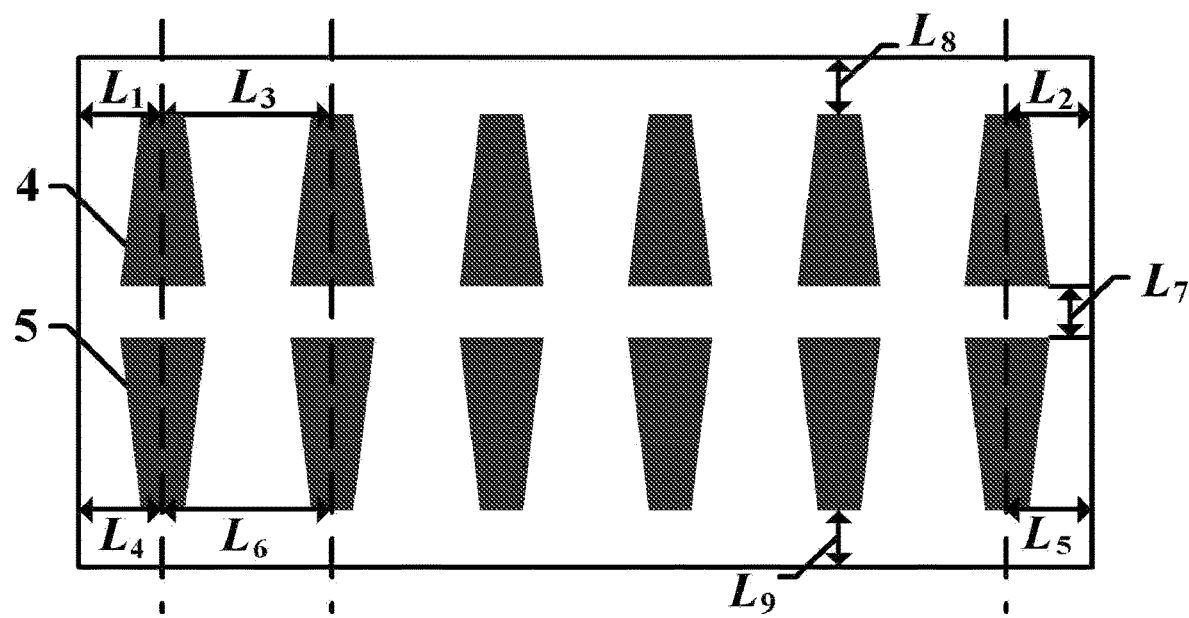
FIG. 2 is a top view of the mid-infrared gas sensor based on a tapered sub-wavelength grating slot waveguide according to the invention.

Embodiment: As shown in FIG. 1 and FIG. 2, a mid-infrared gas sensor based on a tapered sub-wavelength grating slot waveguide comprises a lower cladding 1, a first tapered grating array 2 and a second tapered grating array 3, wherein the lower cladding 1 is a cuboid waveguide and is made of calcium fluoride, a length direction of the lower cladding 1 is a left-right direction, a width direction of the lower cladding 1 is a front-back direction, a thickness direction of the lower cladding 1 is an up-down direction, the lower cladding 1 has a thickness greater than or equal to 6 µm, the first tapered grating array 2 and the second tapered grating array 3 are disposed on an upper surface of the lower cladding 1, and the first tapered grating array 2 is located in front of the second tapered grating array 3.

The first tapered grating array 2 is formed by m identical first core waveguides 4 that are regularly distributed at intervals from left to right. The value of m is 5566. The first core waveguides 4 are tapered waveguides and are made of silicon. Front faces of the first core waveguides 4 are rectangular. Long edges of the front faces of the first core waveguides 4 are in the left-right direction. Wide edges of the front faces of the first core waveguides 4 are in the up-down direction. The long edges of the front faces of the first core waveguides 4 have a length of 784 nm. The wide edges of the front faces of the first core waveguides 4 have a width of 6 μm. Long edges of rear faces of the first core waveguides 4 are in the left-right direction. Wide edges of the rear faces of the first core waveguides 4 is in the up-down direction. The long edges of the rear faces of the first core waveguides 4 have a length of 980 nm. The wide edges of the rear faces of the first core waveguides 4 have a width of 6 μm. Each first core waveguide 4 has four sides. A distance between the front faces and rear faces of the first core waveguides 4 is 1.6 μm. An upper side and a lower side of each first core waveguide 4 are both isosceles trapezoids with a upper base of 784 nm. A lower base of 980 nm and a height of 1.6 μm. Left and right sides of the first core waveguides 4 are rectangular. Wide edges of the left and right sides of the first core waveguides 4 are in the up-down direction and have a width of 6 μm. Two long edges of the left side of each first core waveguide 4 coincide with a left hypotenuse of the upper side of the first core waveguide 4 and a left hypotenuse of the lower side of the first core waveguide 4 in a one-to-one corresponding manner. Two long edges of the right side of each first core waveguide 4 coincide with a right hypotenuse of the upper side of the first core waveguide 4 and a right hypotenuse of the lower side of the first core waveguide 4 in a one-to-one corresponding manner. The front faces of the m first core waveguides 4 are located on a same plane. The rear faces of the m first core waveguides 4 are located on a same plane. The plane where the front faces of the m first core waveguides 4 are located is parallel to a front face of the lower cladding 1. A distance $L_1$ from a bilateral symmetry plane of a leftmost first core waveguide 4 of the m first core waveguides 4 to a left face of the lower cladding 1 is greater than or equal to 980 nm, a distance $L_2$ from a bilateral symmetry plane of a rightmost first core waveguide 4 to a right face of the lower cladding 1 is greater than or equal to 980 nm, and a distance $L_3$ between the bilateral symmetry planes of every two adjacent first core waveguides 4 is 1960 nm.

The second tapered grating array 3 is formed by m identical second core waveguides 5 that are regularly distributed at intervals from left to right. The value of m is 5566, the second core waveguides 5 are tapered waveguides and are made of silicon, rear faces of the second core waveguides 5 are rectangular. Long edges of the rear faces of the second core waveguides 5 are in the left-right direction. Wide edges of the rear faces of the second core waveguides 5 are in the up-down direction. The long edges of the rear faces of the second core waveguides 5 have a length of 784 nm. The wide edges of the rear faces of the second core waveguides 5 have a width of 6 μm. Long edges of front faces of the second core waveguides 5 are in the left-right direction. Wide edges of the front faces of the second core waveguides 5 are in the up-down direction. The long edges of the front faces of the second core waveguides 5 have a length of 980 nm. The wide edges of the front faces of the second core waveguides 5 have a width of 6 μm. A distance between the front faces and the rear faces of the second core waveguides 5 is 1.6 μm. Each second core waveguide 5 has four sides, an upper side and a lower side of each second core waveguide 5 are both isosceles trapezoids with an upper base of 784 nm. A lower base of 980 nm and a height of 1.6 μm, left and right sides of the second core waveguides 5 are rectangular. Wide edges of the left and right sides of the second core waveguides 5 are in the up-down direction and have a width of 6 μm. Two long edges of the left side of each second core waveguide 5 coincide with a left hypotenuse of the upper side of the second core waveguide 5 and a left hypotenuse of the lower side of the second core waveguide 5 in a one-to-one corresponding manner. The front faces of the m second core waveguides 5 are located on a same plane. The rear faces of the m second core waveguides 5 are located on a same plane. The plane where the rear faces of the m second core waveguides 5 are located is parallel to the rear face of the lower cladding 1. A distance $L_4$ from a bilateral symmetry plane of a leftmost second core waveguide 5 of the m second core waveguides 5 to the left face of the lower cladding 1 is greater than or equal to 980 nm, a distance $L_5$ from a bilateral symmetry plane of a rightmost second core waveguide 5 to the right face of the lower cladding 1 is greater than or equal to 980 nm, and a distance between the bilateral symmetry planes of every two adjacent second core waveguides 5 is 1960 nm.

A $L_7$ distance from the plane where the front faces of the m second core waveguides 5 are located to the plane where the rear faces of the m first core waveguides 4 are located is 120 nm; and a distance $L_8$ from the plane where the front faces of the m first core waveguides 4 are located to the front face of the lower cladding 1 is equal to a distance $L_9$ from the plane where the rear faces of the m second core waveguides 5 are located to the rear face of the lower cladding 1, and is greater than or equal to 11.55 μm.

A plane which is parallel to the bilateral symmetry plane of the leftmost first core waveguide in the first tapered grating array, is located on the left of the bilateral symmetry plane of the leftmost first core waveguide in the first tapered grating array, and is 980 nm away from the bilateral symmetry plane of the leftmost first core waveguide in the first tapered grating array is called a first plane. A plane which is parallel to the bilateral symmetry plane of the rightmost first core waveguide in the first tapered grating array, located on the right of the bilateral symmetry plane of the rightmost first core waveguide in the first tapered grating array, and is 980 nm away from the bilateral symmetry plane of the rightmost first core waveguide in the first tapered grating array is called a second plane. A distance between the first plane and the second plane is defined as the length of an effective sensing light path of the mid-infrared gas sensor of the invention. According to the Beer-Lambert law, when the wavelength of a light source covers the characteristic absorption spectral line of a trace gas to be measured, the output light intensity will decline, and the composition and concentration of substances can be determined according to the selective absorption characteristics of different substance molecules, wherein the decline of the light intensity of an output port may be expressed as:

$$I_{out}=I_{in}\exp(-\eta\varepsilon_g C_g L_0-\alpha_{int}L_0) \qquad (1)$$

$I_{out}$ and $I_{in}$ are an output light intensity and an input light intensity respectively, $\varepsilon_g$ is the absorption coefficient of a target gas, $C_g$ is the concentration of the target gas, $L_0$ is an effective sensing light path of the mid-infrared gas sensor, $\alpha_{int}$ is an extrinsic loss of the waveguide in the mid-infrared gas sensor and includes an absorption loss and a scattering loss, and η is a dimensionless parameter and represents the degree of light-substance interaction in an evanescent field. In a spectral absorption-based gas sensor, the greater the dimensionless parameter of light-substance interaction, the more light participating in sensing, and the better the sensing performance.

According to the mid-infrared gas sensor based on a tapered sub-wavelength grating slot waveguide provided by the invention, first, different from traditional slab waveguides and ridge waveguides in the design of the first tapered grating array and the second tapered grating array, large gaps are reserved between the adjacent first core waveguides and the adjacent second core waveguides to allow gas to be filled therein, to enlarge the light-substance interaction area, thus enhancing the light-substance interaction. Moreover, the dielectric interface of a slot structure formed by m first core waveguides and m second core waveguides does not meet the condition of electric displacement continuity, so an electric field is limited to a greater extent in the low-refractivity slot area. The upper sides and lower sides of the first core waveguides and the second core waveguides are all isosceles trapezoids, so guide waves will shift toward the rear faces of the first core waveguides and the front faces of the second core waveguides and will be concentrated between the m first core waveguides in the first tapered grating array and the m second core waveguides in the second tapered grating array, thus enhancing the light-substance interaction. Finally, the first tapered grating array and the second tapered grating array are both of a one-dimensional photonic crystal structure, which will greatly decrease the light velocity in the vicinity of a Brillouin zone boundary under the slow light effect produced by structural chromatic dispersion, to allow photons to fully interact with substances to increase the energy density, thus enhancing the light-substance interaction. By adoption of the mid-infrared gas sensor based on a tapered sub-wavelength grating slot waveguide of the invention, the dimensionless parameter of light-substance interaction may reach 6.1516 under a wavelength of 7.7 μm.

Figure 3:
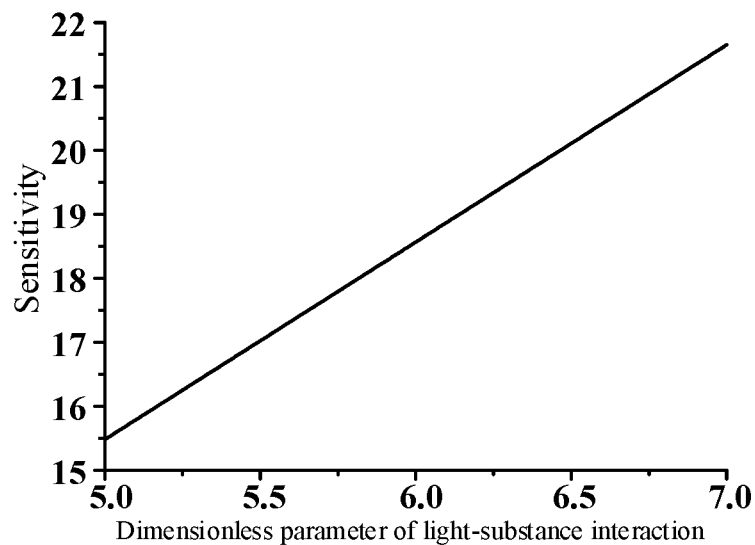
FIG. 3 illustrates a variation curve of the sensitivity of the mid-infrared gas sensor based on a tapered sub-wavelength grating slot waveguide with a dimensionless parameter of light-substance interaction according to the invention.
Figure 4:
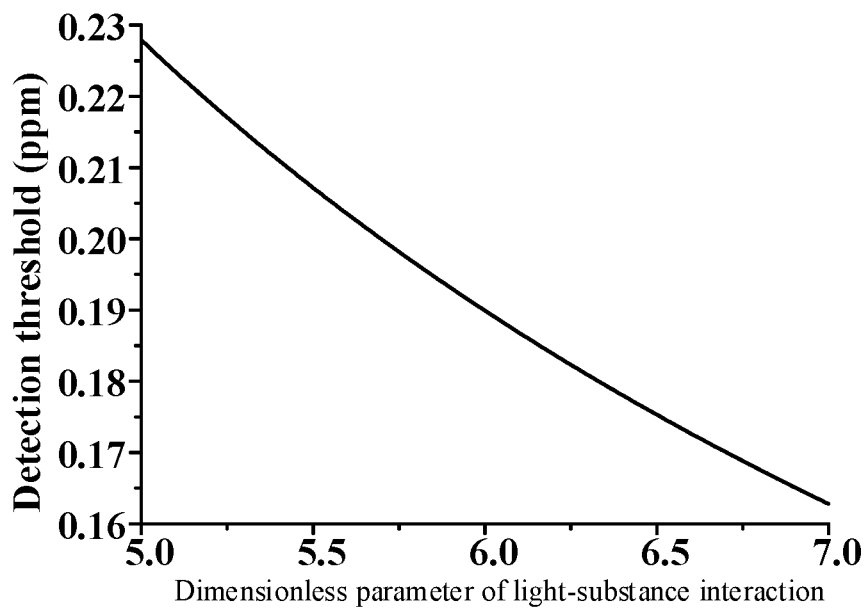
FIG. 4 illustrates a variation curve of the detection threshold of the mid-infrared gas sensor based on a tapered sub-wavelength grating slot waveguide with a dimensionless parameter of light-substance interaction according to the invention.

To verify the superiority of the mid-infrared gas sensor based on a tapered sub-wavelength grating slot waveguide provided by the invention, a differential detection structure, composed of a mid-infrared light source, an optical fiber, an optical gas chamber and a photoelectric detector, is used to test the sensing performance of the mid-infrared gas sensor based on a tapered sub-wavelength grating slot waveguide. The light source adopts quantum cascade lasers (Alpes Lasers) with an output power of 1 mW (7.7 μm, 1290 cm 1), the operating spectral range of the photoelectric detector (Horiba, DSS-MCT14-020L) is 3 μm-12 μm, and the equivalent noise power and bandwidth are $5*10^{-12}$ WHz$^{-1/2}$ and 5 KHz respectively. The single-wavelength and double-light path differential detection structure can split light input by the laser light source into two paths of light with a fixed energy ratio by a light splitter (power splitter). One path of light passes through the optical gas chamber filled with a gas to be detected to fully react with the gas to be detected, and is used as a signal light path. The other path of light is introduced into a reference chamber filled with a balance gas (nitrogen generally), and then is injected into the photoelectric detector to be used as a reference light path. The reference light path can effectively eliminate detection errors caused by fluctuations of the light source and environmental noise in the light propagation process. During the test, methane is used as a target gas, of which the binary diffusion coefficient in air is 0.208 cm$^2$/s, an absorption coefficient sg under the corresponding wavelength is 174 L·mol$^{-1}$·cm$^{-1}$ according to the HITRAN spectrum database, the initial concentration Cg is 50 ppm; the intrinsic loss αint of the waveguide is 4.0 dB/cm, the environmental temperature and pressure are 298.15 K and 100 kPa respectively. The variation curve of the sensitivity of the mid-infrared gas sensor based on a tapered sub-wavelength grating slot waveguide of the invention with the dimensionless parameter of light-substance interaction is shown in FIG. 3, the variation curve of the detection threshold of the mid-infrared gas sensor based on a tapered sub-wavelength grating slot waveguide of the invention with the dimensionless parameter of light-substance interaction is shown in FIG. 4, and the curve of the response time of the mid-infrared gas sensor based on a tapered sub-wavelength grating slot waveguide of the invention is shown in FIG. 5.

The sensitivity is defined as the variation of the normalized output light intensity caused by the change of gas concentration, and the sensing sensitivity will become higher with the increase of the degree of light-substance interaction. As can be known by analyzing FIG. 3, the sensitivity S of the sub-infrared gas sensor of the invention increases gradually with the increase of the dimensionless parameter η of light-substance interaction, and under the wavelength of 7.7 μm, the dimensionless parameter η of light-substance interaction of the sub-infrared gas sensor provided by the invention reaches 6.1516, and the sensing sensitivity is 19.0341. Compared with similar spectral absorption-based waveguide sensors for detecting methane gas, such as the device with the sensing sensitivity of 4.89 disclosed by Literature 1 (Pi, M. et al. Design of a mid-infrared suspended chalcogenide/silica-on-silicon slot-waveguide spectroscopic gas sensor with enhanced light-gas interaction effect. *Sensors Actuators, B Chem.* 297, 126732 (2019).), and the device with the sensing sensitivity of 7.151 disclosed by Literature 2 (Wang, Y. et al. Ultra-high-power-confinement-factor integrated mid-infrared gas sensor based on the suspended slot chalcogenide glass waveguide. Sensors Actuators B Chem. 347, (2021).), the sensitivity of the sub-infrared gas sensor provided by the invention is remarkably improved.

With the increase of the degree of light-substance interaction, more light will contact and react with gas, and the sensing detection threshold will become lower. As can be known by analyzing FIG. 4, the detection threshold Cmin of the mid-infrared gas sensor provided by the invention decreases gradually with the increase of the dimensionless parameter η of light-substance interaction, and under the wavelength 7.7 μm, the dimensionless parameter η of light-substance interaction of the sub-infrared gas sensor of the invention reaches 6.1516, and the detection threshold is 0.18524 ppm. Compared with similar spectral absorption-type waveguide sensors for detecting methane gas, such as the device with a detection threshold of 1.42 ppm disclosed by Literature 3 (Gervais, A., Jean, P., Shi, W. & LaRochelle, S. Design of slow-light subwavelength grating waveguides for enhanced on-chip methane sensing by absorption spectroscopy. IEEE J. Sel. Top. Quantum Electron. 25, (2019).), and the device with a detection threshold of 5.88 ppm disclosed by Literature 4 (Xu, G. et al. Design and analysis of slow-light Bloch slot waveguides for on-chip gas sensing. *J. Opt. Soc. Am. B* 37, 257 (2020).), the mid-infrared gas sensor provided by the invention has a lower detection threshold.

Figure 5:
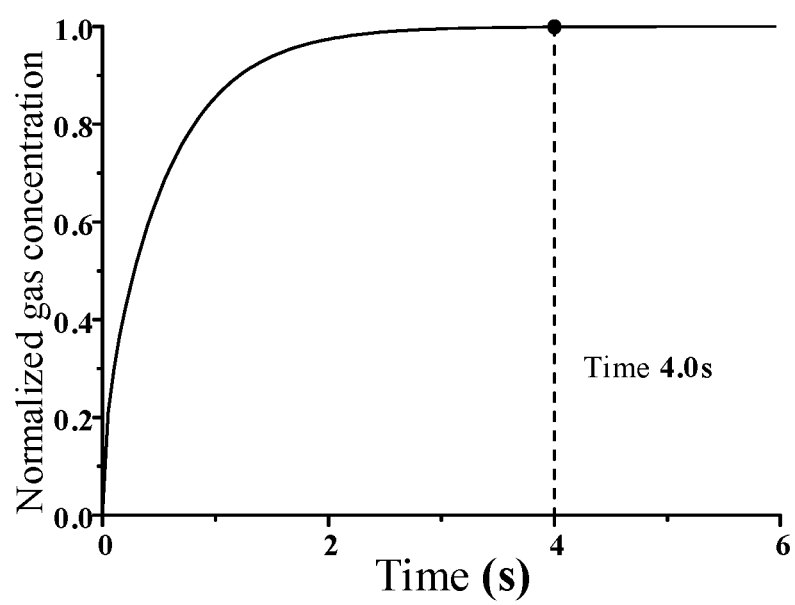
FIG. 5 illustrates a curve of the response time of the mid-infrared gas sensor based on a tapered sub-wavelength grating slot waveguide according to the invention.

As can be known by analyzing FIG. 5, the length of the effective light path of the mid-infrared gas sensor provided by the invention is 1.090936 cm, and when t>4.0 s, the diffusion of gas in the gas chamber has been completed by 99.9% and trends to be stable. So, the response time is 4.0 s when the sub-infrared gas sensor is used to detect methane gas. Compared with similar spectral absorption-type waveguide sensors for detecting methane gas, such as the device with a response time of 10 s disclosed by Literature 5 (Kumari, B., Varshney, R. K. & Pal, B. P. Design of chip scale silicon rib slot waveguide for sub-ppm detection of N2O gas at mid-IR band. *Sensors Actuators, B Chem.* 255, 3409-3416 (2018).), and the device with a response time of 9 s disclosed by Literature 2 (Wang, Y. et al. Ultra-high-power-confinement-factor integrated mid-infrared gas sensor based on the suspended slot chalcogenide glass waveguide. Sensors Actuators B Chem. 347, (2021).), the mid-infrared gas sensor provided by the invention has a shorter response time.

According to the mid-infrared gas sensor based on a tapered sub-wavelength grating slot waveguide provided by the invention, the design of the first tapered grating array and the second tapered grating array enlarges the light-substance interaction area. The upper sides and lower sides of the first core waveguides and the second core waveguides are designed into isosceles trapezoid, so that a light field is more concentrated in a slot structure formed by m first core waveguides and m second core waveguides The scheme that the first tapered grating array and the second tapered grating array are both of a one-dimensional photonic crystal structure effectively increase the energy density between light and substances and thus enhances the light-substance interaction, and the dimensionless parameter of light-substance interaction reaches 6.1516 under a wavelength of 7.7 μm. The differential detection structure eliminates detection errors caused by fluctuations of a light source and environmental noise in the light propagation process and tests the sensing performance of the sensor, and the mid-infrared gas sensor based on a tapered sub-wavelength grating slot waveguide has a sensing sensitivity of 19.0341, a detection threshold of 0.18524 ppm and a response time of 4.0 s. So compared with similar spectral absorption-type waveguide sensors, the mid-infrared gas sensor based on a tapered sub-wavelength grating slot waveguide is high in sensitivity, low in detection threshold and quick in response.

What is claimed is:

1. A mid-infrared gas sensor based on a tapered sub-wavelength grating slot waveguide, comprising a lower cladding, a first tapered grating array and a second tapered grating array, wherein
    the lower cladding is a cuboid waveguide and is made of calcium fluoride, a length direction of the lower cladding is a left-right direction, a width direction of the lower cladding is a front-back direction, a thickness direction of the lower cladding is an up-down direction, the lower cladding has a thickness greater than or equal to 6 μm, the first tapered grating array and the second tapered grating array are disposed on an upper surface of the lower cladding, and the first tapered grating array is located in front of the second tapered grating array;
    the first tapered grating array is formed by m identical first core waveguides that are regularly distributed at intervals from left to right, a value of m is 5566, the first core waveguides are tapered waveguides and are made of silicon, front faces of the first core waveguides are rectangular, long edges of the front faces of the first core waveguides are in the left-right direction, wide edges of the front faces of the first core waveguides are in the up-down direction, the long edges of the front faces of the first core waveguides have a length of 784 nm, the wide edges of the front faces of the first core waveguides have a width of 6 μm, long edges of rear faces of the first core waveguides are in the left-right direction, wide edges of the rear faces of the first core waveguides is in the up-down direction, the long edges of the rear faces of the first core waveguides have a length of 980 nm, the wide edges of the rear faces of the first core waveguides have a width of 6 μm, each first core waveguide has four sides, a distance between the front faces and the rear faces of the first core waveguides is 1.6 μm, an upper side and a lower side of each first core waveguide are both isosceles trapezoids with a upper base of 784 nm, a lower base of 980 nm and a height of 1.6 μm, left and right sides of the first core waveguides are rectangular, wide edges of the left and right sides of the first core waveguides are in the up-down direction and have a width of 6 μm, two long edges of the left side of each first core waveguide coincide with a left hypotenuse of the upper side of the first core waveguide and a left hypotenuse of the lower side of the first core waveguide in a one-to-one corresponding manner, two long edges of the right side of each first core waveguide coincide with a right hypotenuse of the upper side of the first core waveguide and a right hypotenuse of the lower side of the first core waveguide in a one-to-one corresponding manner, the front faces of the m first core waveguides are located on a same plane, the rear faces of the m first core waveguides are located on a same plane, the plane where the front faces of the m first core waveguides are located is parallel to a front face of the lower cladding, a distance from a bilateral symmetry plane of a leftmost first core waveguide of the m first core waveguides to a left face of the lower cladding is greater than or equal to 980 nm, a distance from a bilateral symmetry plane of a rightmost first core waveguide to a right face of the lower cladding is greater than or equal to 980 nm, and a distance between the bilateral symmetry planes of every two adjacent first core waveguides is 1960 nm;
    the second tapered grating array is formed by m identical second core waveguides that are regularly distributed at intervals from left to right, the value of m is 5566, the second core waveguides are tapered waveguides and are made of silicon, rear faces of the second core waveguides are rectangular, long edges of the rear faces of the second core waveguides are in the left-right direction, wide edges of the rear faces of the second core waveguides are in the up-down direction, the long edges of the rear faces of the second core waveguides have a length of 784 nm, the wide edges of the rear faces of the second core waveguides have a width of 6 μm, long edges of front faces of the second core waveguides are in the left-right direction, wide edges of the front faces of the second core waveguides are in the up-down direction, the long edges of the front faces of the second core waveguides have a length of 980 nm, the wide edges of the front faces of the second core waveguides have a width of 6 μm, a distance between the front faces and the rear faces of the second core waveguides is 1.6 μm, each second core waveguide has four sides, an upper side and a lower side of each second core waveguide are both isosceles trapezoids with an upper base of 784 nm, a lower base of 980 nm and a height of 1.6 μm, left and right sides of the second core waveguides are rectangular, wide edges of the left and right sides of the second core waveguides are in the up-down direction and have a width of 6 μm, two long edges of the left side of each second core waveguide coincide with a left hypotenuse of the upper side of the second core waveguide and a left hypotenuse of the lower side of the second core waveguide in a one-to-one corresponding manner, two long edges of the right side of each second core waveguide coincide with a right hypotenuse of the upper side of the second core waveguide and a right hypotenuse of the lower side of the second core waveguide in a one-to-one corresponding manner, the front faces of the m second core waveguides are located on a same plane, the rear faces of the m second core waveguides are located on a same plane, the plane where the rear faces of the m second core waveguides are located is parallel to the rear face of the lower cladding, a distance from a bilateral symmetry plane of a leftmost second core waveguide of the m second core waveguides to the left face of the lower cladding is greater than or equal to 980 nm, a distance from a bilateral symmetry plane of a rightmost second core waveguide to the right face of the lower cladding is greater than or equal to 980 nm, and a distance between the bilateral symmetry planes of every two adjacent second core waveguides is 1960 nm;

a distance from the plane where the front faces of the m second core waveguides are located to the plane where the rear faces of the m first core waveguides are located is 120 nm; and a distance from the plane where the front faces of the m first core waveguides are located to the front face of the lower cladding is equal to a distance from the plane where the rear faces of the m second core waveguides are located to the rear face of the lower cladding, and is greater than or equal to 11.55 μm.

\* \* \* \* \*